United States Patent [19]

Moasser

[11] Patent Number: 4,646,725

[45] Date of Patent: Mar. 3, 1987

[54] METHOD FOR TREATING HERPES LESIONS AND OTHER INFECTIOUS SKIN CONDITIONS

[76] Inventor: Manoutchehr Moasser, 16005 Crain Hwy., Brandywine, Md. 20613

[21] Appl. No.: 552,314

[22] Filed: Nov. 16, 1983

[51] Int. Cl.⁴ ............................................. A61H 1/00
[52] U.S. Cl. .................................... 128/24 A; 128/32
[58] Field of Search ................................ 128/24 A, 32

[56] References Cited

U.S. PATENT DOCUMENTS

| | | | |
|---|---|---|---|
| 2,283,285 | 5/1942 | Pohlman | 128/24 A |
| 2,752,914 | 7/1956 | Pohlman | 128/24 A |
| 2,852,019 | 9/1958 | Fry | 128/24 A |
| 2,876,764 | 3/1959 | Guttner | 128/24 A |
| 2,917,042 | 12/1959 | Brown et al. | 128/24 A |
| 2,920,617 | 1/1960 | Boiarsky | 128/24 A |
| 3,102,535 | 9/1963 | Dailey | 128/24 A |
| 3,358,677 | 12/1967 | Sheldon | 128/24 A |
| 3,828,769 | 8/1974 | Mettler | 128/24 A |
| 4,040,414 | 8/1977 | Suroff | 128/24 A |
| 4,073,289 | 2/1978 | Fahim | 128/24 A |
| 4,269,176 | 5/1981 | Beyer | 128/24 A |
| 4,309,989 | 1/1982 | Fahim | 128/24 A |
| 4,372,296 | 2/1983 | Fahim | 128/24 A |
| 4,484,569 | 11/1984 | Diller | 128/660 |

FOREIGN PATENT DOCUMENTS

| | | |
|---|---|---|
| 1085064 | 7/1954 | France . |
| 694194 | 10/1979 | U.S.S.R. . |
| 731962 | 5/1980 | U.S.S.R. . |
| 770496 | 10/1980 | U.S.S.R. . |

OTHER PUBLICATIONS

Biosonik; High–Intensity Ultrasonic Probe.

*Primary Examiner*—Clyde I. Coughenour
*Attorney, Agent, or Firm*—Sixbey, Friedman & Leedom

[57] ABSTRACT

The present invention provides a method for treating infectious skin conditions characterized by the presence of lesions and local or systemic symptoms such as pain, itching, burning or swelling. Infections caused by herpes viruses and staphylococcal bacteria have been shown to be particularly responsive to the present method and apparatus, although the treatment of a wide range of infectious and inflammatory skin disorders is contemplated to fall within the scope of the present invention. The present method comprises the direct application of ultrasonic radiation to the affected body area for a time and at a power output sufficient to provide rapid symptomatic relief and promote rapid healing.

2 Claims, 3 Drawing Figures

METHOD FOR TREATING HERPES LESIONS AND OTHER INFECTIOUS SKIN CONDITIONS

TECHNICAL FIELD

The present invention relates generally to a method and apparatus for treating infectious skin conditions and specifically to a method of applying ultrasonic radiation with a specially designed ultrasound adapter to skin lesions caused by Herpes viruses and other infectious agents.

BACKGROUND ART

The treatment of lesions of the skin and mucous membranes caused by infectious agents typically consists of applying a chemotherapeutic agent topically to the lesions or systemically to provide symptomatic relief to the patient. When the causative agent is known and a specific medication is available against that particular agent, the medication is generally prescribed with satisfactory results. However, the causative agent is not always known nor can it always be readily identified so that agent-specific therapy can be utilized to treat the lesions as soon as possible after they appear so that maximum relief is afforded the patient. Even if the causative agent can be quickly identified and a specific drug of choice is available for immediate use, use of that particular drug may be contraindicated for specific patients. Such a situation commonly arises, for example, when penicillin is the drug of choice against a particular infectious agent, and the infected patient is allergic to penicillin. The patient's discomfort is then prolonged by a search for an acceptable substitute drug, during which time the only therapy likely to be available is palliative at best. When the causative agent cannot be identified or when there is no specific drug available for treatment against a known infectious agent, the discomfort to the patient resulting from the infection is not likely to be alleviated quickly.

The situation described above is particularly likely to occur in the case of infections caused by the several herpes viruses. Confirmation of the infectious agent as herpes can be time consuming, and, in the interim the infected patient may undergo considerable discomfort from the painful local vesicles and systemic symptoms which accompany herpes infections. Although various drugs have been proposed which seem to be partially effective against the herpes virus, these drugs are either not available in the United States or are available only on an experimental basis. However, therapeutic action is still nonconclusive. The drugs and treatments available for symptomatic relief of herpes lesions, typically analgesics and anesthetics for the relief of pain, have only limited efficacy and do not affect the lesions themselves.

Other, local, treatments for lesions caused by herpes viruses have been proposed; however, each has its drawbacks. For example, painting genital herpes lesions with acridine dyes and then exposing them to light carries the danger that the inactivated viruses could transform normal cells into potentially malignant cells. U.S. Pat. No. 4,309,989 to Fahim describes a local treatment of herpes lesions which applies an antiviral drug to the lesions with ultrasonic vibrations to cause the drug to penetrate the tissues. While this treatment may be more effective than some other available treatments, the available antiviral drugs disclosed for use with this process are not completely free from problems. For example, idoxuridine is generally recognized as effective primarily against herpes caused keratitis, and interferon is still highly experimental, very expensive and difficult to obtain. Moreover, drug-resistant viruses are being observed, which limits the efficacy of these drugs.

The use of various ultrasound generating apparatus and the application of ultrasonic radiation or ultrasound is disclosed in the prior art for many diverse purposes. U.S. Pat. Nos. 2,283,285 to Pohlman; 2,917,042 to Brown et al; 3,102,535 to Dailey; 3,828,769 to Mettler and 4,269,176 to Beyer et al all teach the use of ultrasound to provide symptomatic relief for musculoskeletal disorders. U.S. Pat. Nos. 4,040,414 to Suroff and 4,372,296 to Fahim describe the use of ultrasound in the treatment of acne, while U.S. Pat. No. 4,073,289 to Fahim discloses the sterilization of male domestic animals by using ultrasound. U.S. Pat. No. 4,309,989, discussed hereinabove, discloses the use of ultasound to massage an antiviral agent into lesions caused by herpes viruses. None of the aforementioned patents, however, teaches the use of ultrasonic radiation alone to provide rapid symptomatic relief and to promote the quick healing of lesions of the skin and mucous membranes caused by infectious agents such as bacteria and viruses.

The prior art, therefore, has failed to suggest a satisfactory method or apparatus for treating infectious skin conditions, particularly those caused by herpes viruses, which quickly and effectively alleviates the underlying symptoms accompanying these conditions and which treats the manifestations of the infectious condition as well.

SUMMARY OF THE INVENTION

It is a primary object of the present invention, therefore, to provide a method and apparatus for treating infectious skin conditions which provides rapid and effective alleviation of the underlying symptoms as well as treatment of the condition itself.

It is another object of the present invention to provide a method for treating infectious skin conditions which includes the direct application of ultrasonic radiation to the lesions caused by the infectious condition, thereby causing such lesions to heal and the discomfort associated with such lesions to disappear.

It is yet another object of the present invention to provide a method for treating infections of the skin and mucous membranes caused by herpes viruses wherein ultrasonic radiation is applied directly to the herpetic lesions.

It is a further object of the present invention to provide apparatus for attachment to a source of ultasonic radiation whereby the ultrasonic radiation may be concentrated and applied to a specific individual lesion for the direct application of ultasound only to that lesion in the treatment of an infectious skin condition characterized by such lesions.

It is still another object of the present invention to provide apparatus for attachment to a source of ultrasonic radiation including a plurality of disposable treatment heads having treatment areas of varying sizes, wherein a treatment head of a specific size is selected to apply the maximum amount of ultrasonic radiation to the area to be treated, thus avoiding unnecessarily exposing the surrounding areas to ultrasonic radiation.

Other objects and advantages will be apparent from an examination of the claims and drawings.

In accordance with the aforesaid objects a method and apparatus for applying ultrasonic radiation to treat the underlying symptoms and manifestations of infectious conditions of the skin and mucous membranes is provided. The present method includes the direct application of ultrasonic radiation to the individual lesions or to areas of several lesions in close proximity associated with the infectious condition. Application of the ultrasonic radiation to treat such conditions is optimally achieved by the present apparatus, which includes base means for attachment to a source of ultrasonic radiation, reducer means for engaging the base means and for receiving disposable adapter means. The reducer means includes fluid receiving means for receiving the coupling fluid or gel required for the transmission of ultrasonic radiation. The disposable adapter means includes a lower threaded portion which is received in corresponding mating threads in the reducer means. The upper, treatment head portion of the adapter means includes an open treatment area whereby an appropriate amount of coupling fluid may be extruded through the open treatment area to provide the transmission of ultrasonic radiation to a lesion or an area of skin corresponding to the size of the open treatment area of the adapter means. A plurality of disposable adapter means having different size open treatment areas is provided so that an appropriate adapter means can be selected for the optimum application of ultrasonic radiation in each individual case.

BEST MODE FOR CARRYING OUT THE INVENTION

Figure 1:
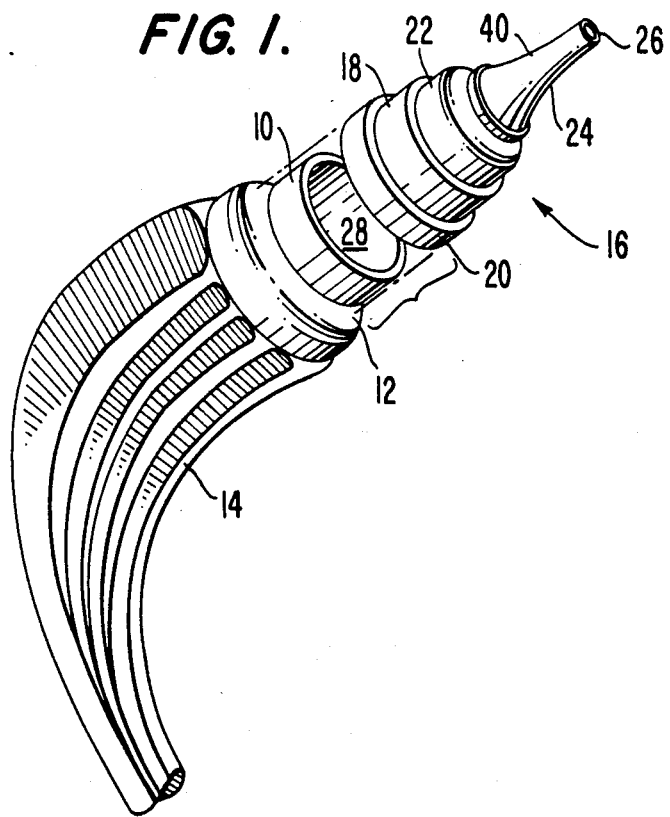
FIG. 1 shows in perspective view the ultrasonic treatment apparatus of the present invention positioned just above the head of an ultrasonic vibrator.

Infectious skin conditions can affect the skin and mucous membranes of an infected patient in a variety of ways. For example, staphylococcal or streptococcal infections of the skin may manifest themselves as pustules, ulcers or other lesions of varying surface areas and depths. Infections caused by herpes viruses are typically characterized by vesicles or blisters or by ulcers which may occur singly or in clusters. Herpetic lesions are almost always accompanied by pain and a burning sensation, and itching may be present. The type of herpes virus causing the infection generally determines the area of the body where the lesions occur. Herpes zoster, for example, causes the formation of lesions commonly known as "shingles" in the cutaneous areas, usually on the trunk of the body, supplied by the peripheral sensory nerves which arise in the root ganglion infected by the virus. Herpes simplex, on the other hand, produces lesions in either the oral or genital area of the body, depending on which viral serotype is the infectious agent. Oral herpetic lesions, often referred to as fever blisters or canker sores, are found on the lips or face and inside the mouth. Genital herpetic lesions may be found anywhere on the external or internal genitalia and surrounding skin, as well as inside the urethra. Consequently, local treatment of lesions caused by Herpes simplex viruses can be difficult. Left untreated, Herpes simplex lesions usually heal by themselves in about 7 to 14 days, with those lesions in moist areas healing slowly. However, during this period, the infected patient may experience discomfort ranging from itching and burning to excruciating pain. The pain accompanying Herpes zoster infections can become particularly severe.

The method and apparatus of the present invention have been found to relieve the underlying symptoms of herpetic and other infectious lesions of the skin and mucous membranes while simultaneously promoting healing of the lesions. Patients treated by the present method and apparatus have experienced symptomatic relief, which in many cases can be characterized as dramatic, as well as rapid healing of the infectious lesions. The method and apparatus of the present invention, moreover, have greatly facilitated the direct treatment of infectious lesions like those caused by the Herpes simplex virus which occur in such difficult to reach areas as the inside of the mouth, the urethra, the vagina and the cervix. It has been found that the direct application of ultrasonic radiation to infectious lesions of the skin and mucous membranes causes these lesions to heal more rapidly and effectively than with previous treatment methods and, in addition, simultaneously relieves the untoward symptoms which typically accompany such lesions.

As will be described in more detail in the case histories presented below, ultrasonic radiation is applied directly to the infected area at a power level and for a period of time which may vary from case to case and which will depend on such factors as the severity of the lesions and the treatment area of the ultrasound adapter selected for use. There are many conventional ultrasonic generators available on the market which will provide the power output requirements necessary to treat infectious skin conditions according to the present method. Since ultrasonic radiation cannot be transmitted through air, an appropriate coupling fluid is provided to conduct the ultrasonic radiation from the ultrasonic generator to the area to be treated. Any commercially available inert coupling fluid, preferably in gel form, can be used to assure proper ultrasound transmission. In practicing the present method, a thin layer of coupling fluid is positioned between the ultrasound adapter treatment area and the lesion or lesions to be treated, and the ultrasound applicator is then moved over the lesion or lesions for the time required to affect treatment.

Figure 2:
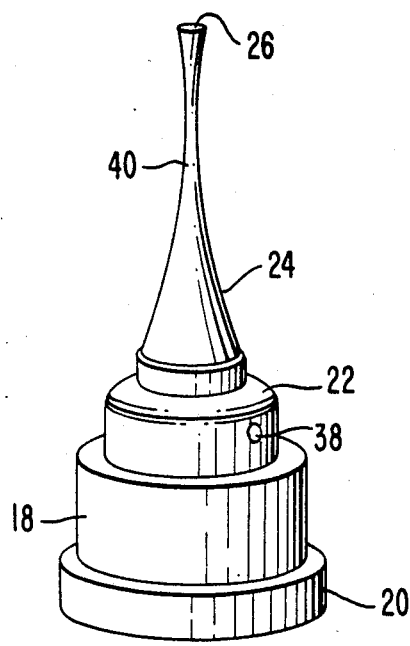
FIG. 2 shows the ultrasonic treatment apparatus of the present invention in front view.
Figure 3:
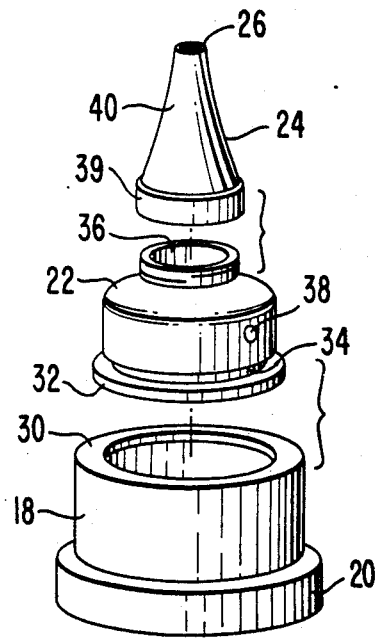
FIG. 3 shows the ultrasonic treatment apparatus of the present invention in an exploded perspective.

Because the location of many infectious lesions rendered the direct application of ultrasound according to the present method impossible with available ultrasonic applicators, a highly versatile disposable ultrasonic radiation application apparatus has been developed which greatly facilitates the treatment of any infectious lesion, despite its location. The apparatus of the present invention can be conveniently adapted to fit on any conventional ultrasound treatment head to render it able to effectively apply ultrasonic radiation to infectious lesions in areas which would normally be inaccessible to conventional ultrasound applicators. FIGS. 1 to 3 show the present ultrasonic treatment apparatus.

Referring to the drawings, the head of a conventional ultrasonic vibrator is shown at 10. This head is shown supported by a support structure 12, which receives supply cable 14 and provides a connection between, supply cable 14 and head 10. Supply cable 14 is connected at its opposite end (not shown) to a source of ultrasonic radiation (not shown). The present ultrasonic applicator 16 includes three sections which fit together and fit over the head 10 to reduce the ultrasound output area and to concentrate the ultrasonic radiation. Base section 18, which includes an annular collar 20 along its lower edge snaps over head 10 to provide a secure connection between the cable 14 and the base 18.

A central reducer section 22 is engaged along one side by the upper edge of base 18 in a manner which will be explained in more detail hereinbelow. The central reducer section 22 receives in its opposite side an adapter portion 24 which may vary in length to produce a treatment area 26 having a desired diameter. The diameter of treatment area 26 is substantially smaller than the diameter of treatment surface 28 on head 10.

The diameter of base 18 corresponds substantially to the diameter of treatment surface 28 on head 10. Base 18 is preferably formed from a plastic material which is sufficiently rigid to support the reducer and adapter sections, but which also has some flexibility. The diameter of the top edge of base 18 is effectively reduced by providing an annular flange 30, which is shown in FIG. 3. Reducer section 22 is provided with an annular lip 32 and an annular groove 34. Lip 32 fits underneath flange 30 so that flange 30 is engaged in groove 32. This structure holds reducer section firmly in base 18 without the need for clips or other fastening elements. Reducer section 22 also includes in the side opposite lip 32 a threaded opening 36 having a diameter significantly smaller than the diameter of lip 32. An additional opening 38 is located in the wall of central reducer section 22 for receiving ultrasound coupling fluid. Central reducer section 22 is preferably formed from a soft, somewhat flexible, rubber or plastic material.

Adapter 24, which is the terminal end of the present apparatus, is threadedly engaged in opening 36 of reducer 22. The outside diameter of the threaded area 39 of adapter 24 corresponds to the diameter of opening 36. Because one of the objects of the present apparatus is to provide an ultrasound treatment surface suitable for applying ultrasonic radiation to very small areas, the diameter of treatment area 26 will vary according to the area to be treated. Additionally, the length of the shaft 40 of adapter 24 will vary as required to reduce the diameter of treatment area 26. Shaft 40 in FIG. 2, for example, is shown to be more elongated than is shaft 40 in FIGS. 1 and 3, and treatment area 26 in FIG. 2 has a correspondingly smaller diameter than in FIGS. 1 and 3. Adapter 24 will ideally be made from a relatively rigid plastic material which is inexpensive so that the adapter portion can be disposable rather than requiring sterilization between ultrasound applications. Although the adapter 24 is not intended to contact the lesions being treated directly, contact may occasionally occur which could contribute to the spread of the infection.

In operation, the desired adapter 24 is selected, the treatment apparatus 16 is assembled and snapped over the ultrasound head 10. A coupling fluid, preferably in gel form, is introduced into opening 38, and reducer section 22 may be squeezed, if necessary, to distribute the coupling fluid so that a bead of fluid is formed outside treatment area 26. The ultrasound apparatus is then applied to the lesion or area to be treated, maintaining a layer of the coupling fluid between the tip of the adapter and the area being treated. Use of the present adapter apparatus concentrates the ultrasound radiation on a smaller affected area, for example a single lesion, than was heretofore possible and produces a higher temperature than that achieved by a conventional ultrasound head. Temperatures at the treatment surface up to 30 degrees F. higher were recorded when the present ultrasound adapter was used. Additionally, beneficial treatment results were observed in a shorter time when the ultrasound treatment was applied with the present apparatus than when a conventional ultrasonic head was used. Although the exact reasons for the excellent results obtained by the present method and apparatus are not fully understood and require further study, initial tests indicate that bacterial growth, at least, is inhibited by the application of ultrasonic radiation with the apparatus described herein.

The following case histories demonstrate the superior results achieved by the present method and apparatus.

Case No. 1

An 11 year old black male was seen with a severe staphylococcal infection of the lips and the skin surrounding the nose and mouth which had been unresponsive to treatment for about one month. Ultrasound was applied to the affected area at a power output of 1.5 watts per square centimeter for 3.0 minutes. The patient was free from infection within 24 hours.

Case No. 2

A 51 year old black male was seen with chest pains related to multiple blisters on the chest and back characteristic of Herpes zoster. The area was treated with ultrasound at a power output of 1.5 watts per square centimeter for 3.0 minutes. Marked improvement and dryness of the blisters was noted 1 day later and recovery was complete within 4 days.

Case No. 3

A 31 year old black female was seen with a large herpetic blister formation on her upper lip to which ultrasound was applied at 1.5 watts per square centimeter for 3.0 minutes. After about 30 minutes the pain and swelling subsided, and the following day the lesions were dry.

Case No. 4

An 83 year old white female suffering from a great deal of pain had a large area of blisters under her right arm from the middle of her chest to the middle of her back caused by a Herpes zoster infection. The area was cleaned and ultrasound was applied for 3.0 minutes at 1.5 watts per square centimeter. Relief of the pain and healing of the blisters was noted within 3 days.

Case No. 5

A 62 year old white female was seen complaining of severe pain on the lower left side of the abdomen. Examination revealed a large area of herpetic blisters which were cleaned and treated with ultrasound at 1.5 watts per square centimeter for 3.0 minutes. The next day the area was dry, and there was no swelling or pain. Within 3 days the lesions showed remarkable improvement.

Case No. 6

A 32 year old female was seen with many herpetic vesicles on the labia majora. Following the application of ultrasound for 3.0 minutes at 1.5 watts per square centimeter, all vesicles disappeared, the edema subsided and the patient complained only of a discharge for the next few days.

Case No. 7

A 26 year old white female was seen for a few fever blisters on her mid-upper lip accompanied by pain and burning. The application of ultrasound at 1.5 watts per square centimeter for 3.0 minutes resulted in the disappearance of all the fever blisters plus the pain and burning in a few hours.

Case No. 8

An 85 year old white male was seen with several small blisters on his lips and ears which had caused swelling and pain. The application of ultrasound at 1.5 watts per square centimeter for 2.0 minutes resulted in the drying of the lesions and the absence of pain and swelling by the following day.

Case No. 9

A 30 year old white female was seen with 2 small painful fever blisters on the lips. Ultrasound treatment at 1.5 watts per square centimeter was applied for 2.0 minutes. Within 24 hours the blisters were completely dried and almost gone.

Case No. 10

A 23 year old white female complaining of pain and itching was seen with fever blisters of the left upper lip. Induration of the vesicles was noted. Ultrasound was applied at 1.5 watts per square centimeter for 3.0 minutes. Symptomatic relief was achieved within about 10 minutes, and the blisters had dried and begun to be scaly within the next few hours.

Case No. 11

A 42 year old white female was seen with a herpetic infection of the right upper lip which had been present for several days. The patient complained of fever, pain and a burning sensation. Ultrasound was applied to the lesions at 1.5 watts per square centimeter for 3.0 minutes. Relief of the pain occurred within 3 hours following treatment, and the blisters had disappeared by the next day.

In Cases Nos. 1-6 the area to be treated was relatively large and was effectively treated with a conventional ultrasound applicator like head 10 of FIG. 1. Since treatment surface 28 of head 10 presents a solid flat surface, coupling fluid, preferably in gel form, must be applied to surface 28 prior to treatment to permit the transmission of ultrasonic radiation to the area being treated. An ultrasound power output of 1.5 watts per square centimeter applied for a treatment time of about 3.0 minutes was found to be most effective. However, the power output and treatment time can be varied from these levels depending on the size of the area and the severity of the lesions to be treated.

In Cases Nos. 7-11 above, the ultrasound applicator apparatus 16 shown in FIGS. 1 to 3 was secured to a conventional ultrasound treatment like head 10 in FIG. 1. In these cases, the area of lesions requiring treatment was smaller than in Cases Nos. 1-6, and it was highly desirable to be able to concentrate the ultrasound radiation only on the infected area, thus avoiding the unnecessary application of radiation to the surrounding healthy tissue. Although in all of these cases a power output of 1.5 watts per square centimeter was used a lesser output, in the range of 1.0 to 1.5 watts per square centimeter could also be used effectively, particularly with an adapter 24 like that shown in FIG. 2 having a treatment opening 26 which is less than 1.0 millimeter in diameter. A treatment time of 2 to 3 minutes has been found to be adequate to achieve the rapid relief of symptoms and healing experienced in the cases described above. However, this parameter, too, could be varied as required in individual cases. It will be noted that the use of the present adapter apparatus accelerated symptomatic relief and healing, producing relief and promoting healing within a matter of hours.

The structure of the disposable adapter 24 greatly facilitates treatment. Sufficient coupling fluid or contacting gel can be inserted into opening 38 to maintain a bead of gel between the treatment opening 26 and the lesion being treated during the treatment period. Moreover, because adapter 24 is disposable, it can be removed easily following treatment of an individual lesion or infected area and discarded. A new adapter can be quickly screwed into the reducer section 22 and another infected area of the same patient can then be treated without any risk of autoinnoculation. This feature of the present apparatus can be particularly important and helpful for example, in cases where a single patient requires treatment for both oral and genital herpes during a single treatment session and it is desired to take every precaution to confine each type of virus to its original area of infection. Further, the provision of very small treatment openings 26 in combination with a very slender elongated adapter shaft 40 and the coupling fluid reservoir within reducer section 22 enables very precise direction of ultrasonic radiation and assures a sufficient supply of coupling fluid to guarantee transmission of the ultrasonic radiation. Lesions, such as those found in the urethra, vagina and buccal mucosa, which are impossible to reach with conventional ultrasound applicators can now be treated very precisely and effectively.

INDUSTRIAL APPLICABILITY

The present method and apparatus will find its primary application in the treatment of infectious skin conditions, such as those caused by herpes viruses and staphyloccal bacteria. Such infections have been successfully treated with the present method and apparatus. In addition, noninfective skin conditions such as psoriasis have responded to the treatment described herein, and it is contemplated that the direct application of ultrasonic radiation according to the present method and using the present apparatus will find widespread application and provide beneficial results in a variety of infectious and inflammatory conditions of the skin and mucous membranes.

I claim:

1. A method for substantially eliminating from the skin and mucous membranes herpetic lesions caused by virus of the herpes type comprising directly contacting each said herpetic lesion with a concentrated source of ultasonic radiation having a focused effective area from an ultrasound generator in the absence of an antiviral agent for a period of time within the range of 2.0 to 3.0 minutes at a power output of 1.5 watts per square centimeter.

2. A method for treating herpes virus infections characterized by the presence of localized herpetic lesions and local or systemic discomfort and distress comprising the steps of:
   a. attaching apparatus having a treatment tip for reducing the effective area through which ultrasonic radiation is emitted and focusing the effective area of the ultrasonic radiation to concentrate said radiation on each herpetic lesion to a conventional ultrasound treatment head;

b. introducing coupling fluid free from antiviral agents into said apparatus and manipulating said apparatus to produce a bead of said fluid at the treatment tip of said apparatus;

c. directly contacting each of the herpetic lesions to be treated with the bead of coupling fluid formed at said treatment tip so that each said herpetic lesion is within the area of the bead;

d. applying ultrasonic radiation produced by an ultrasound generator directly to each said herpetic lesion at a power output of 1.0 to 1.5 watts per square centimeter for a time period of 2.0 to 3.0 minutes; and e. removing said treatment tip from said lesion and disposing of said treatment tip.

* * * * *